United States Patent [19]

Millar

[11] Patent Number: 4,678,463

[45] Date of Patent: Jul. 7, 1987

[54] DEVICES FOR INSERTION INTO A BODY CAVITY OF AN ANIMAL AND/OR APPLICATORS THEREFOR

[76] Inventor: Thomas D. Millar, 10 Menzies Place, Hamilton, New Zealand

[21] Appl. No.: 908,890

[22] Filed: Sep. 16, 1986

Related U.S. Application Data

[63] Continuation of Ser. No. 706,942, Mar. 1, 1985, abandoned.

[30] Foreign Application Priority Data

Mar. 1, 1984 [NZ] New Zealand .................. 207341

[51] Int. Cl.⁴ ............................................. A61M 31/00
[52] U.S. Cl. ...................................... 604/285; 128/130
[58] Field of Search ................ 604/285, 890, 55; 128/127–133

[56] References Cited

U.S. PATENT DOCUMENTS

| | | | |
|---|---|---|---|
| 3,515,132 | 12/1967 | McKnight | 128/130 |
| 3,811,423 | 5/1974 | Dickinson, III et al. | 128/127 |
| 3,835,863 | 9/1974 | Goldberg et al. | 604/284 |
| 3,991,750 | 11/1976 | Vickery | 128/130 |
| 3,993,057 | 11/1976 | Ramwell | 604/55 |
| 4,066,075 | 1/1978 | Hughes | 604/890 |
| 4,145,408 | 3/1979 | Laughlin | 604/890 |
| 4,353,363 | 10/1982 | Quesada | 128/130 |

*Primary Examiner*—John D. Yasko
*Attorney, Agent, or Firm*—Holman & Stern

[57] ABSTRACT

A device for insertion into a body cavity of an animal and for producing a controlled rate of release of chemicals into the body of the animal, has a spine with a body and legs hinged to the body, the spine being coated with a coating incorporating therein a material impregnated with one or more chemical impregnants which leach therefrom when exposed to body fluids, the legs being of a size foldable in a manner such that the cross sectional area and cross sections dimensions of the combined folded legs when in a folded position are substantially the same as the cross sectional area and dimensions of the body of the device.

An applicator is provided for inserting the device, the applicator having a shaft with a handle at one end and an open ended tube at the other end, the open ended tube having an open ended slot in the walls of said passageway with the open end of the slot at or near the open end of the tube and a discharging device comprising a rod having an operating member connected to the rod through a member which will enable the rod to be mounted within the open ended passageway with the operating member outside the tube so that on the device being fitted in a folded condition within the tube, the expelling device is operable to expel the device from the applicator after the applicator and device have been inserted in a body cavity of an animal.

6 Claims, 7 Drawing Figures

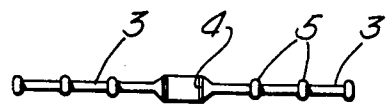
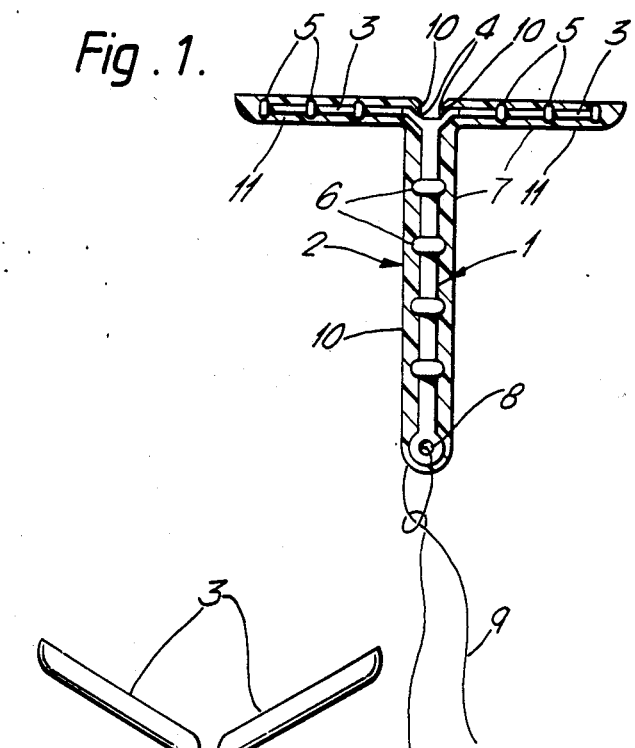
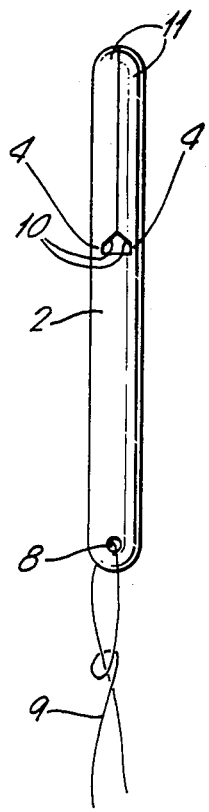
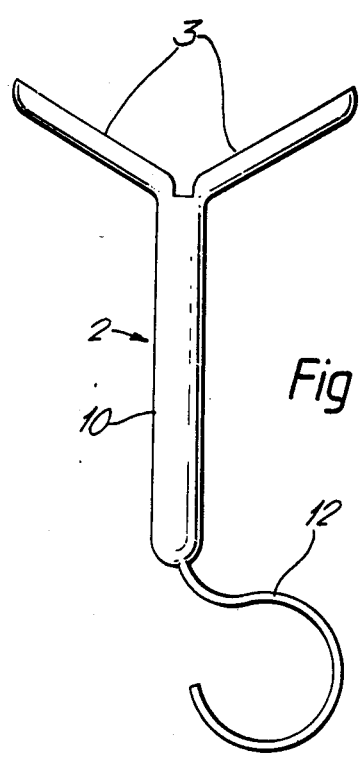

DEVICES FOR INSERTION INTO A BODY CAVITY OF AN ANIMAL AND/OR APPLICATORS THEREFOR

This is a continuation of application Ser. No. 706,942, filed Mar. 1, 1985 now abandoned.

This invention relates to insertion into a body cavity e.g vagina of an animal devices and/or applicators therefor and has been devised particularly though not solely for use for the placing and subsequent use of the devices for the controlled release of drugs or trace elements contained in the device in relation to non-parous ewes.

It is an object of the present invention to provide an intravaginal device and/or applicator therefor and/or a combination of such a device and an applicator which will at least provide the public with a useful choice.

Accordingly in one aspect the invention may broadly be said to consist in a device for insertion into a body cavity of an animal and for producing a controlled rate of release of chemicals into the body of the animals, said device comprising a spine having a body member and a plurality of leg members hinged to said body, the spine being coated with a coating having at least some of the coating forming part of the surface thereof or incorporated therein an impregnated material impregnated with one or more chemical impregnants which are adapted to leach therefrom when exposed to body fluids, said plurality of coated leg members being of a size such and being foldable in a manner such that the cross sectional area and cross sections dimensions of the combined bolded plurality of leg members when in a folded position are substantially the same as the cross sectional area and dimensions of the coated body member of the device.

In a further aspect the invention may broadly be said to consist in an applicator for inserting a device into a body cavity of an animal said applicator comprising a shaft having a handle at one end and an open ended tube at the other end, said open ended tube having an open ended slot in the walls of said passageway with the open end of the slot at or near the open end of the tube and a discharging device comprising a rod having an operating member connected to said rod through a member which will enable the rod to be mounted within the open ended passageway with the operating member outside the tube so that on an intravaginal device being fitted in a folded condition within said tube, said expelling device is operable to expel the intravaginal device from the applicator after the applicator and device have been inserted in the vagina of an animal.

In non-parous ewes in most or at least many breeds of sheep there is a constricting band of connective tissue situated within the vagina and an orifice through the restricting band is of approximately 10 mm diameter. This will vary slightly e.g. larger and smaller than 10 mm diameter, but in all cases offers a severe limitation in the size of any intravaginal device which may be used with or inserted into the ewe.

Existing intravaginal devices such as progesterone loaded sponges and the CIDR dispensers (controlled Internal Drug Release) which may be used for oestrus synchronisation and are the subject of New Zealand Patent Application numbers 193976 and 200564 are unsuitable for non-parous ewes as they are too large in cross section to pass through the restricted orifice of non-parous ewes without damage to the ewes A survey of a range of non-parous ewes shows that approximately 98% will comfortably accept the passage of an object of at least 10.5 mm diameter while the remainder will almost all accept the passage of an object of at least 9.0 mm. It is accepted that a device of 11.0 maximum diameter may be used after immersion in a suitable veterinary lubricant.

Non-parous ewes with a vaginal restriction of less than say 9.0 mm would not be suitable for the insertion of such a device.

The invention described herein at least in the preferred form obviates or minimises the aforementioned difficulties by providing an intravaginal device and applicator which together can be made so as not to exceed the above upper size or dimentral limit and the intravaginal device is easily withdrawn when required.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

One preferred form of the invention will now be described with reference to the accompanying drawings in which:

FIG. 1 is a cross section of an intravaginal device according to the invention shown in an "open" attitude;

FIG. 2 shows the devices of FIG. 1 in a "closed" disposition as for insertion;

Figure 5:
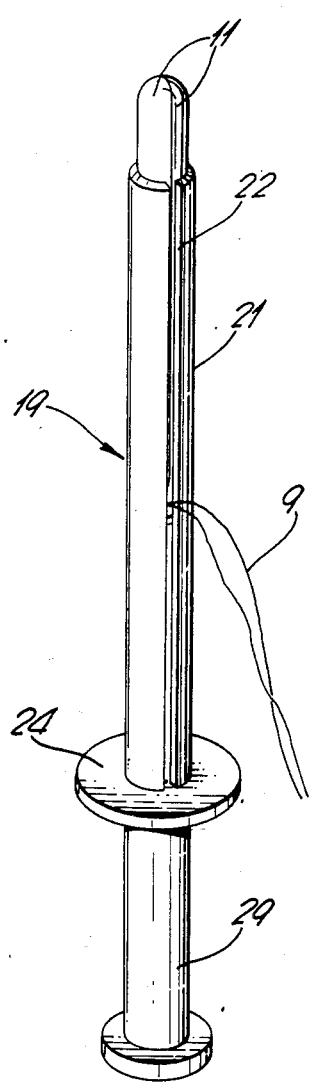

FIG. 3 details of hinges forming part of a spine of the device of FIGS. 1 and 2;

FIG. 4 is a plan view of a different form of the device shown in FIGS. 1 to 3;

FIG. 5 shows a device of FIGS. 1 to 3 loaded into the inserter of FIG. 4 for placement in an animal.

Figure 6:
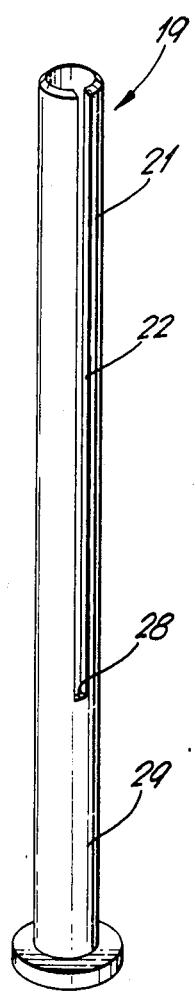
Figure 7:
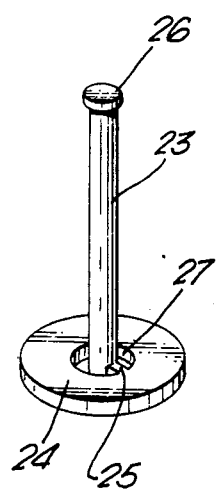

FIG. 6 is a perspective sketch of a suitable inserter;

FIG. 7 shows a release plunger for the inserter of figure.

Referring to the drawings, a form of intravaginal device is shown in FIG. 1 in which a flexible spine 1 includes a main body member 2 and a plurality of and preferably two leg members 3, hinged to 2 by means of integral resiliently flexible hinges 4.

A clearance space 10 is provided on the inner faces of the leg members adjacent the hinges 24 to assist easy closure of the leg members towards each other.

Protrusions 5 on legs 3 and 6 on member 2 assist in locating and retaining the polymer skin or coating 7 which covers all three parts of the spine, the polymer coating 7 providing a drug carrying and releasing matrix. An eyelet 8 at the outer end of main body member 2 allows for the insertion and fixing of withdrawal string or filament 9.

Alternatively, as shown in FIG. 4, a withdrawal filament 12 may be provided integral with the moulded skin or coating 7 on the main body member 2 but preferably integral with the spine 1.

The spine 1 may be moulded of a suitable non-toxic and flexible thermoplastics such as nylon or polypropylene, preferably a thermoplastic with a relatively high heat deflection temperature to resist deformation during curing of a liquid silicone if this is used for the drug carrying matrix or to resist heat distortion during injection moulding if another thermoplastic such as EVA is used for the drug carrying matrix.

The coating of drug carrying polymer is so shaped that the portion of polymer skin 7 surrounding member 2 is of circular cross section and of typically 9.0 mm diameter though this dimension may be adjusted according to the use to which the device is to be put and may be larger for e.g. parous ewes or cows.

The polymer coating 11 around legs 3 are of semi-circular cross section so that when the two coated spine legs 3 are folded together as shown in FIG. 2, they will form a combined circular cross section and of cross sectional dimensions which will form an extension of coating 7 on members 2 and be of approximately the same external diameter. There could be more than two say three coated legs 3 so shaped as to fold to a circular cross section and again of substantially the same combined cross sectional dimensions as the main body 2. Typically coated member 2 will be longer than coated legs 3, for example coated member 2 about 60 mm in length and coated legs 3 about 30 mm in length.

The folded device as in FIG. 2 will be placed in an applicator 19 shown in FIGS. 5 to 7 so that about 15 mm of the polymer coating 11 on the shorter coated legs 3 protrude from the open end of the inserter as shown in FIG. 5. This dimension is not critical provided enough of short legs 3 is placed inside the applicator to retain the legs 3 of the device in a folded attitude.

The applicator 19 for the above device is shown in FIG. 6 and is formed from a thin walled tube 21 of metal or moulded plastic with a slot 22 to receive the withdrawal filament 9 of the intravaginal device and the applicator has a smooth and rounded open end.

A plunger to expel the device into the vagina is shown in FIG. 7 and comprises a rod 23 having a cap 26, the rod 23 being fixed to or integral with a disc 24 in which there is an opening 27 with a radial link 25 joining the disc 24 and rod 27.

In use the rod 23 and cap 26 are slid into tube 21 with tube 21 passing through the opening 27 in disc 24 and the radial link 25 placed in slot 22.

The cap 26 on the other end of rod 23 rests against the end of the device 1 remote from the eye 3 so that when the device is correctly placed in the tube 21, link 25 rests on the lower end 28 of slot 22.

The loaded device and the end of the inserter are then dipped in or otherwise coated with a suitable lubricating/disinfecting fluid and placed into the vagina of the animal. Disc 24 provides a conventient depth reference.

Disc 24 is then held agains the vulva lips and tube 21 withdrawn by means of grip 29 on the lower end of tube 21 sufficiently to release the device into the vagina.

The inserter is then removed.

The legs 3 now expend to the disposition shown in FIG. 1 or FIG. 4 due to the resilience of the hinges 4.

Withdrawal of the device is simply effected by pulling on filament 29 which remains protruding from the animal's vulva.

The short arms 11 will fold at hinges 4 to allow safe and comfortable withdrawal.

The hinges 4 provide an important aspect of the invention, permitting easy folding to permit insertion of the device 1 into the applicator 19 and then permitting easy folding of the legs 3 when removal is to be effected.

Although described above as being a device particularly though not solely for use in non porous ewes, we have also proved that is is also efficacious with other animals e.g. parous ewes and goats e.g. Angora or Cashmere.

What is claimed is:

1. A device for insertion into the vaginal cavity of an animal and for producing a controlled rate of release of chemicals into the body of the animal, said device comprising a spine having a body and two leg members hinged to said body, each leg member of said spine being hinged to said body by a separate integral stiffly resilient flexible hinge with a clearance space between inner faces of said leg members to assist each closure of said leg members towards each other, the spine being covered with a non-erodable matrix having at least some of the matrix forming part of the surface thereof or the matrix having incorporated therein an impregnated material impregnated with one or more chemical impregnants which are adapted to leach therefrom when exposed to body fluids, said covered leg members being of a size and foldable in a manner such that the cross sectional area and cross sections dimensions of the combined folded leg members when in a folded position are substantially the same as the cross sectional area and dimensions of the coated body of the device, said device having a withdrawal filament attached to said body at the end remote from said hinges.

2. A device as claimed in claim 1 wherein said matrix on said body is formed to a circular cross section.

3. A device as claimed in claim claim 2 wherein two said leg members are provided and the coating on each leg member is formed to a semi circular cross section positioned so that the combination of leg members has a circular cross section.

4. A device as claimed in claim 3 wherein clearance spaces are provided on the inner faces of the leg members adjacent said hinges.

5. An applicator for inserting a device into the vaginal cavity of an animal said applicator comprising a shaft having a handle at one end and an open ended tube at the other end, said open ended tube having an open ended slot in the walls of said passageway with the open end of the slot at or near the open end of the tube and a discharging device comprising a rod having an operating member connected to said rod through a member which will enable the rod to be mounted within the open ended passageway with the operating member outside the tube so that a device according to any one of claims 1 to 4 being fitted in a folded condition within said tube, said expelling device is operable to expel the intravaginal device from the applicator after the applicator and device have been inserted in a body cavity of an animal.

6. The combination of a device according to any one of claims 1 to 5 and an applicator according to claim 5.

* * * * *